(12) United States Patent
Wallenstein et al.

(10) Patent No.: US 8,343,164 B2
(45) Date of Patent: Jan. 1, 2013

(54) IMPLANT INSERTION TOOL

(75) Inventors: Todd Wallenstein, Ashburn, VA (US);
Adam Wassinger, Reston, VA (US);
Peter Harris, Boca Raton, FL (US)

(73) Assignee: K2M, Inc., Leesburg, VA (US)

( * ) Notice: Subject to any disclaimer, the term of this patent is extended or adjusted under 35 U.S.C. 154(b) by 322 days.

(21) Appl. No.: 12/739,507

(22) PCT Filed: Oct. 23, 2008

(86) PCT No.: PCT/US2008/080907
§ 371 (c)(1),
(2), (4) Date: Apr. 23, 2010

(87) PCT Pub. No.: WO2009/055541
PCT Pub. Date: Apr. 30, 2009

(65) Prior Publication Data
US 2010/0262199 A1 Oct. 14, 2010

Related U.S. Application Data

(60) Provisional application No. 60/999,945, filed on Oct. 23, 2007.

(51) Int. Cl.
*A61B 17/88* (2006.01)
(52) U.S. Cl. .................................. 606/99; 606/86 R
(58) Field of Classification Search .............. 606/90, 606/99, 100, 104, 86 A, 86 B, 205–208; 600/218–220, 222; 623/17.11–17.16
See application file for complete search history.

(56) References Cited

U.S. PATENT DOCUMENTS

| | | | |
|---|---|---|---|
| 3,758,849 A | 9/1973 | Susman et al. | |
| 4,309,777 A | 1/1982 | Patil | |
| 4,349,921 A | 9/1982 | Kuntz | |
| 4,602,533 A | 7/1986 | Dunn | |
| 4,714,649 A | 12/1987 | Edwards | |
| 4,743,256 A | 5/1988 | Brantigan | |
| 4,759,766 A | 7/1988 | Buettner-Janz et al. | |
| 5,020,519 A * | 6/1991 | Hayes et al. | 606/237 |
| 5,192,327 A | 3/1993 | Brantigan | |
| 5,425,772 A | 6/1995 | Brantigan | |

(Continued)

OTHER PUBLICATIONS

International Search Report from counterpart International Appln. No. PCT/US2008/080907 mailed Dec. 23, 2008.

(Continued)

*Primary Examiner* — Todd Manahan
*Assistant Examiner* — Jessica Weiss
(74) *Attorney, Agent, or Firm* — Carter, DeLuca, Farrell & Schmidt, LLP

(57) ABSTRACT

An apparatus for inserting a spinal implant includes a first elongate member and a second elongate member operatively connected to each other. The first elongate member includes a first jaw member disposed at a distal portion thereof. The first jaw member defines a first longitudinal axis. The second elongate member includes a second jaw member disposed at a distal portion thereof. The second jaw member defines a second longitudinal axis. The first and second elongate members are adapted to move the first and second jaw members between a first position where the first and second longitudinal axes are oriented substantially parallel to each other and a second position where the first and second longitudinal axes are oriented at an acute angle with respect to each other. The apparatus further includes a locking mechanism adapted to fix a relative position of the first and second elongate members.

31 Claims, 13 Drawing Sheets

U.S. PATENT DOCUMENTS

| | | | |
|---|---|---|---|
| 5,431,658 A | 7/1995 | Moskovich | |
| 5,522,899 A | 6/1996 | Michelson | |
| 5,599,279 A | 2/1997 | Slotman et al. | |
| 5,609,635 A | 3/1997 | Michelson | |
| 5,772,661 A | 6/1998 | Michelson | |
| 5,776,199 A | 7/1998 | Michelson | |
| 5,888,222 A | 3/1999 | Coates et al. | |
| 5,899,901 A | 5/1999 | Middleton | |
| 5,906,616 A | 5/1999 | Pavlov et al. | |
| 6,017,342 A * | 1/2000 | Rinner | 606/57 |
| 6,245,108 B1 | 6/2001 | Biscup | |
| 6,325,827 B1 | 12/2001 | Lin | |
| 6,447,544 B1 | 9/2002 | Michelson | |
| 6,447,547 B1 | 9/2002 | Michelson | |
| 6,478,800 B1 | 11/2002 | Fraser et al. | |
| 6,478,823 B1 | 11/2002 | Michelson | |
| 6,551,316 B1 | 4/2003 | Rinner et al. | |
| 6,569,168 B2 | 5/2003 | Lin | |
| 6,610,089 B1 | 8/2003 | Liu et al. | |
| 6,616,671 B2 | 9/2003 | Landry et al. | |
| 6,676,703 B2 | 1/2004 | Biscup | |
| 6,755,841 B2 | 6/2004 | Fraser et al. | |
| 6,770,074 B2 | 8/2004 | Michelson | |
| 6,986,772 B2 | 1/2006 | Michelson | |
| 7,066,961 B2 | 6/2006 | Michelson | |
| 7,070,598 B2 | 7/2006 | Lim et al. | |
| 7,081,118 B2 | 7/2006 | Weber et al. | |
| 7,087,055 B2 | 8/2006 | Lim et al. | |
| 7,419,505 B2 | 9/2008 | Fleischmann et al. | |
| 7,431,723 B2 | 10/2008 | Hazebrouck | |
| 7,445,637 B2 | 11/2008 | Taylor | |
| 7,462,182 B2 | 12/2008 | Lim | |
| 7,474,240 B2 | 1/2009 | Barrenscheen | |
| 7,481,812 B2 | 1/2009 | Frey et al. | |
| 7,485,120 B2 | 2/2009 | Ray | |
| 7,563,264 B2 | 7/2009 | Landry et al. | |
| 2003/0149438 A1 | 8/2003 | Nichols et al. | |
| 2004/0002758 A1 | 1/2004 | Landry et al. | |
| 2005/0021042 A1 | 1/2005 | Marnay et al. | |
| 2005/0113842 A1 | 5/2005 | Bertagnoli et al. | |
| 2005/0119665 A1 | 6/2005 | Keller | |
| 2005/0154395 A1 | 7/2005 | Robbins et al. | |
| 2005/0165408 A1 | 7/2005 | Puno et al. | |
| 2006/0030856 A1 | 2/2006 | Drewry et al. | |
| 2006/0030862 A1 | 2/2006 | De Villiers et al. | |
| 2006/0052793 A1 | 3/2006 | Heinz | |
| 2006/0195097 A1 | 8/2006 | Evans et al. | |
| 2006/0241641 A1 | 10/2006 | Albans et al. | |
| 2006/0241643 A1 | 10/2006 | Lim et al. | |
| 2006/0247645 A1 | 11/2006 | Wilcox et al. | |
| 2007/0123903 A1 | 5/2007 | Raymond et al. | |
| 2007/0123904 A1 | 5/2007 | Stad et al. | |
| 2007/0191857 A1 | 8/2007 | Allard et al. | |
| 2007/0213722 A1 | 9/2007 | Jones et al. | |
| 2007/0233143 A1 | 10/2007 | Josse et al. | |
| 2007/0233152 A1 | 10/2007 | Stad et al. | |
| 2008/0077153 A1 | 3/2008 | Pernsteiner et al. | |
| 2008/0287957 A1 | 11/2008 | Hester et al. | |
| 2008/0306488 A1 | 12/2008 | Altarac et al. | |
| 2009/0030422 A1 | 1/2009 | Parsons et al. | |

OTHER PUBLICATIONS

"Luminary™ ALIF Disc preparation and implant insertion instruments," Technique Guide, Synthese Spine, Aug. 2006; 22 pages.

* cited by examiner

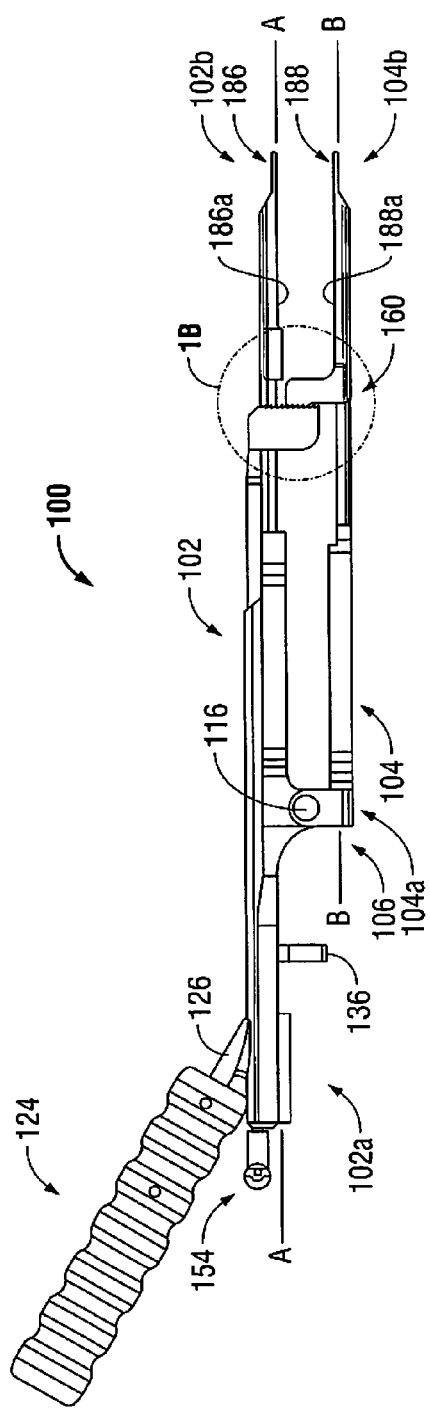
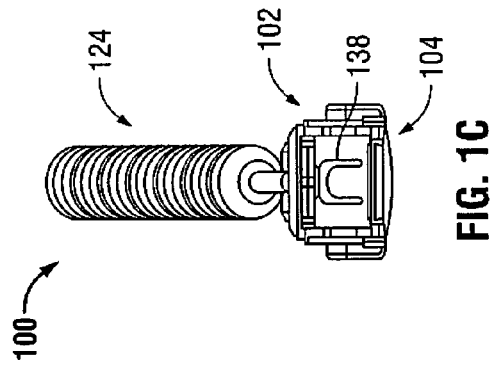
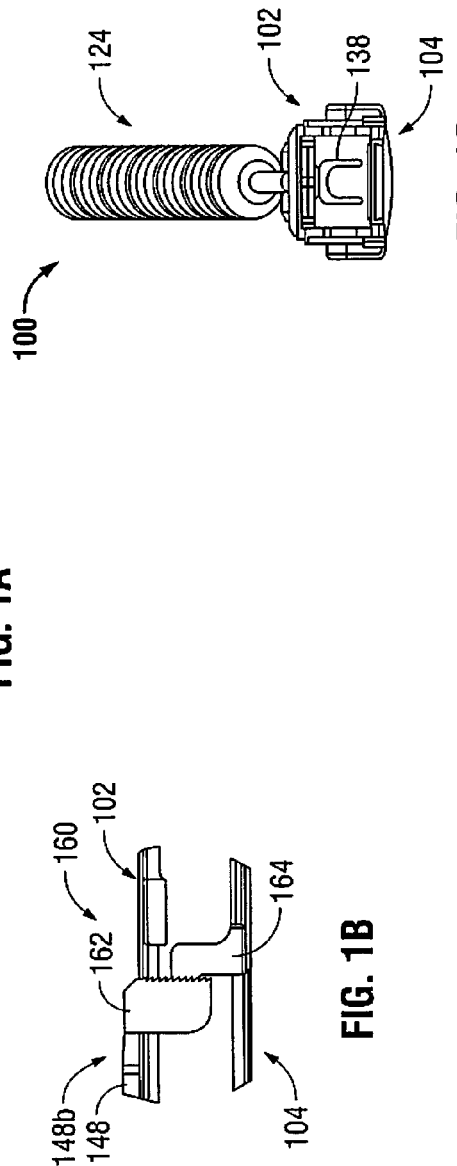

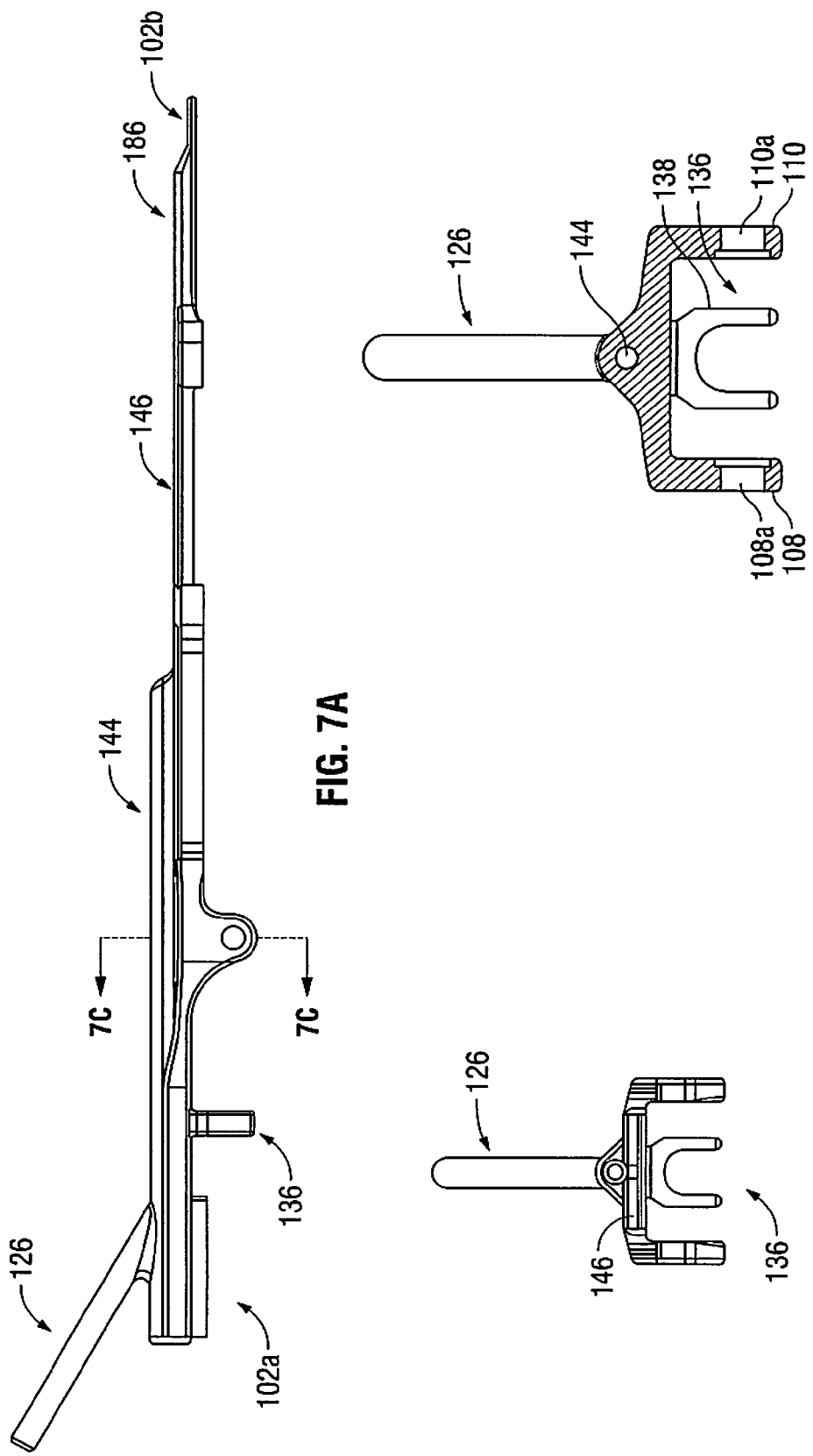

IMPLANT INSERTION TOOL

CROSS-REFERENCE TO RELATED APPLICATION

The present application is a national stage application of International Patent Application PCT/US2008/080907, filed Oct. 23, 2008 which claims priority to, and the benefit of, U.S. Provisional Patent Application Ser. No. 60/999,945, filed on Oct. 23, 2007, the entire contents of which are hereby incorporated by reference.

BACKGROUND

1. Technical Field

The present disclosure relates generally to orthopedic spinal surgery and, in particular, to an apparatus or sled and methods for its use during spinal surgery.

2. Background of Related Art

Intervertebral discs can degenerate over time. In some instances, the disk material is simply diseased. These unfortunate occurrences can lead to, among other things, a reduction in normal intervertebral height. In addition, degenerated or diseased intervertebral disks abnormally compress opposing discs when the disk material is diseased. This unusual compression often results in persistent pain.

Doctors and scientists have developed several techniques to alleviate the pain caused by diseased intervertebral disk material. For instance, stabilization or arthrodesis of the intervertebral joint can reduce the pain associated with movement of an intervertebral joint having diseased disk material. These techniques, also generally known as spinal or joint fusion, entail removing the disk material that separates opposing vertebra and packing the void area with a suitable bone support matrix. The matrix fuses with the bone material of the vertebra thereby joining the two opposing vertebra together.

Joint fusion typically involves the use of a fusion device, such as a spinal cage, an I-beam spacer, or an interbody silo. During fusion procedures, surgeons place a spinal cage in a recess formed between opposing vertebra. This recess usually extends through the cortical end plates of this vertebra. Most spinal cages, as well as other fusion devices, have a chamber, or another kind of suitable space, where bone chips, bone slurry, bone allograft, or any other suitable bone support matrix is placed for facilitating bony union between the vertebrae. Ultimately, this bony union promotes stabilization of vertebrae. Alternatively, the fusion device may be made from autologous bone or allograft bone.

Spinal fusion is typically supported by implanting one or more interbody silos into the disk space either using an anterior or posterior approach. An anterior approach requires a separate incision whereby the surgeon accesses the patient's spine through the abdomen. One advantage is the interbody silo used in this procedure closely matches the footprint of the adjacent vertebral bodies. The disadvantage is that an anterior procedure is typically performed at a different time and requires its own incision and access. The device and methods of the present disclosure may also find application to insertion of non-fusion implants, including but not limited to artificial disc replacement implants.

SUMMARY

The present disclosure relates to an apparatus for inserting a spinal implant, such as an interbody device, between vertebral bodies. This apparatus includes a first elongate member including a first jaw member disposed at a distal end thereof and a second elongate member including a second jaw member disposed at a distal end thereof. The second elongate member is operatively connected to the first elongate member. The first jaw member defines a first longitudinal axis and the second jaw member defines a second longitudinal axis. The first and second elongate members are configured to move the first and second jaw members between a first position and a second position. In the first position, the first and second longitudinal axes are oriented substantially parallel to each other. In the second position, the first and second longitudinal axes are oriented at an acute angle with respect to each other. The apparatus further includes a locking mechanism adapted to fix the relative position of the first and second elongate members. This locking mechanism has first and second sections. The first section is slidably disposed on the first elongate member, and the second section is affixed to the second elongate member.

BRIEF DESCRIPTION OF THE DRAWINGS

Embodiments of the presently disclosed sled are disclosed herein with reference to the drawings wherein:

FIG. 1A is a side elevational view of a sled according to an embodiment of the present disclosure;

FIG. 1B is a front view of the sled shown in FIG. 1A;

FIG. 1C is an enlarged side view of detail A of the sled shown in FIG. 1A;

FIG. 7A is a side elevational view of a first elongate member of the sled shown in FIG. 1A;

FIG. 7B is a front view of the first elongate member shown in FIG. 7A;

FIG. 7C is a front cross-sectional view of the first elongate member shown in FIG. 7A taken along section line D-D of FIG. 7A;

DETAILED DESCRIPTION OF THE EMBODIMENTS

Figure 1D:
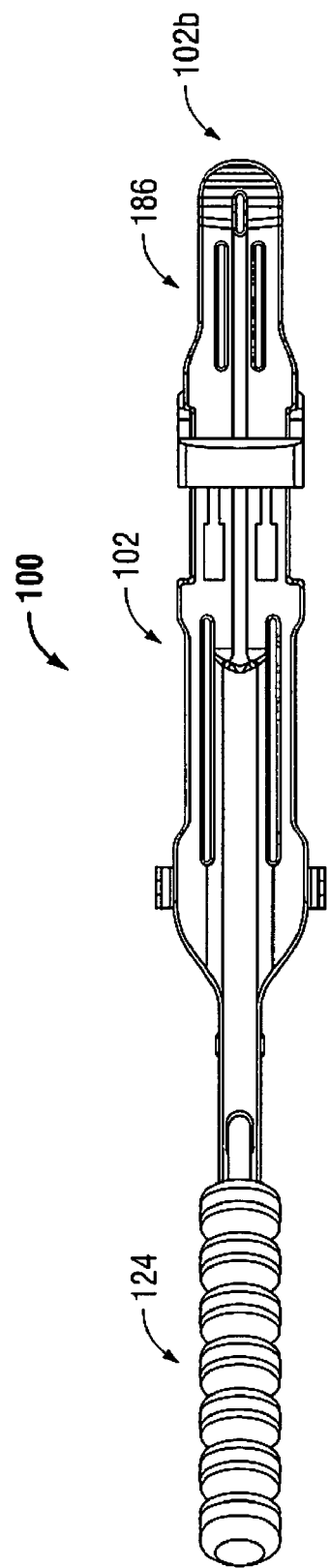
FIG. 1D is a top view of the sled shown in FIG. 1A.
Figure 1E:
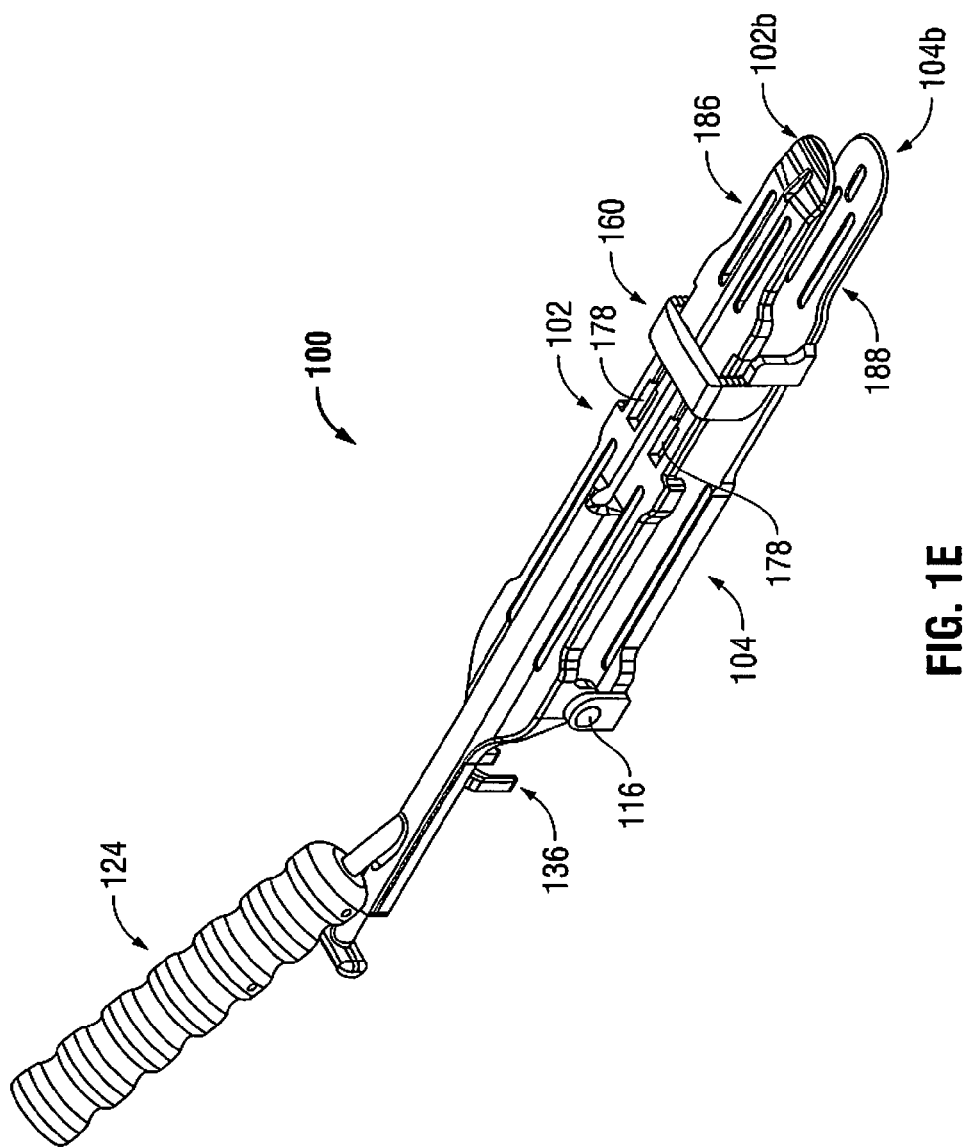
FIG. 1E is a perspective view of the sled shown in FIG. 1A.

Embodiments of the presently disclosed sled will now be described in detail with reference to the drawings in which like reference numerals designate identical or corresponding elements in each of the several views. In the description, the term "proximal" will refer to the portion of the sled that is closest to the operator, while the term "distal" will refer to the portion of the sled that is farthest from the operator.

Referring to FIGS. 1A-1F, an apparatus or a sled for inserting spinal implants or the like is generally shown as 100. Sled 100 includes first and second elongate members 102, 104 operatively connected to each other. First elongate member 102 includes a first jaw member 186 disposed at a distal end 102b thereof, whereas the second elongate member 104 includes a second jaw member 188 disposed at a distal end 104b thereof. First jaw member 186 has a first a longitudinal axis A defining a first plane therealong. Second jaw member 188 has a second longitudinal axis B defining a second plane therealong. First and second elongate members 102, 104 are configured to move first and second jaw members 186, 188 between a first position and second position. In the first position, distal portions 102b, 104b of respective first and second longitudinal axes A,B are oriented substantially parallel to each other, while in the second position, the first and second longitudinal axes A, B are oriented at an acute angle with respect to each other.

Figure 7D:
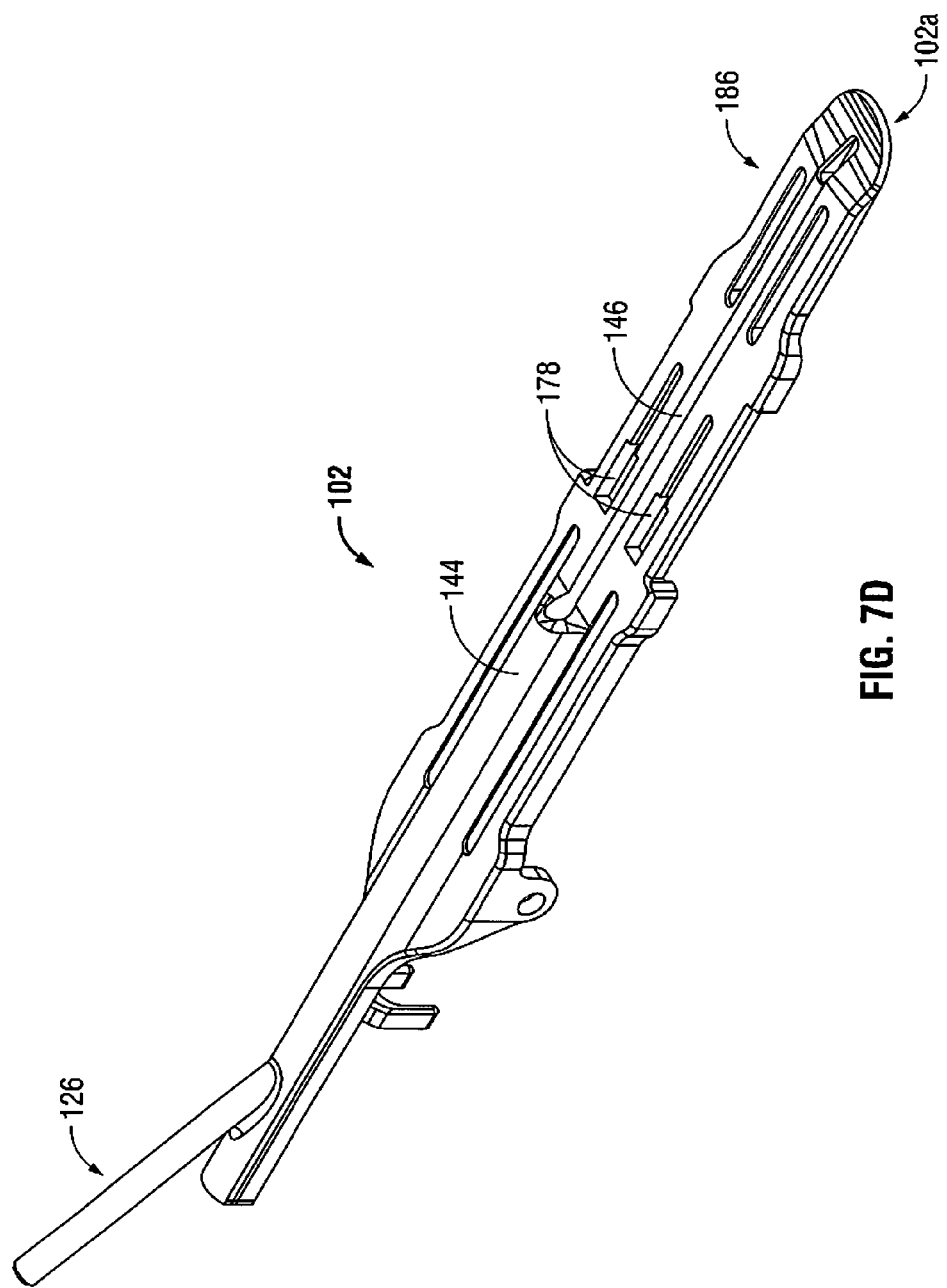
FIG. 7D is a perspective view of the first elongate member shown in FIG. 7A.
Figure 7E:
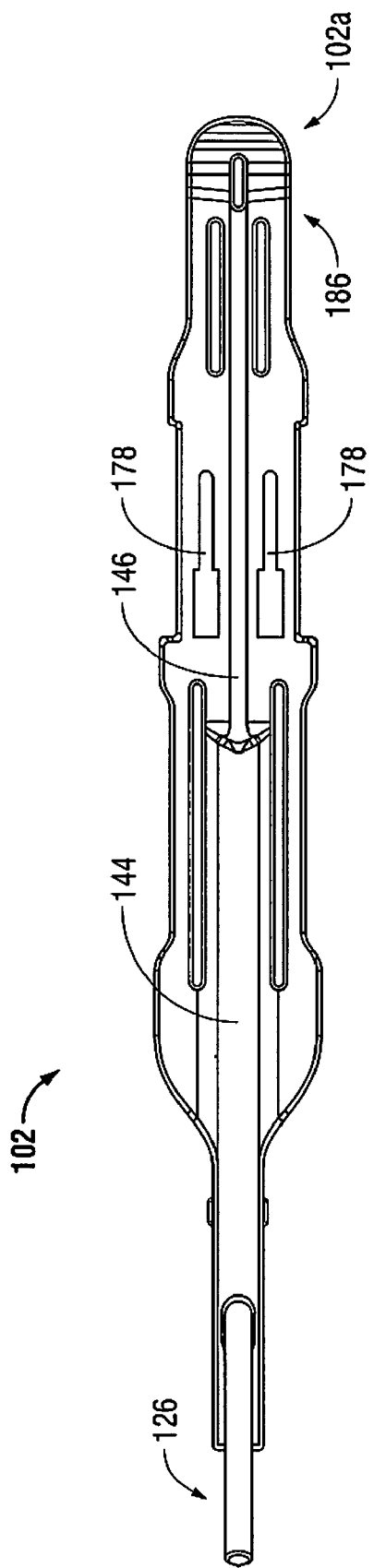
FIG. 7E is a top view of the first elongate member shown in FIG. 7A.
Figure 8A:
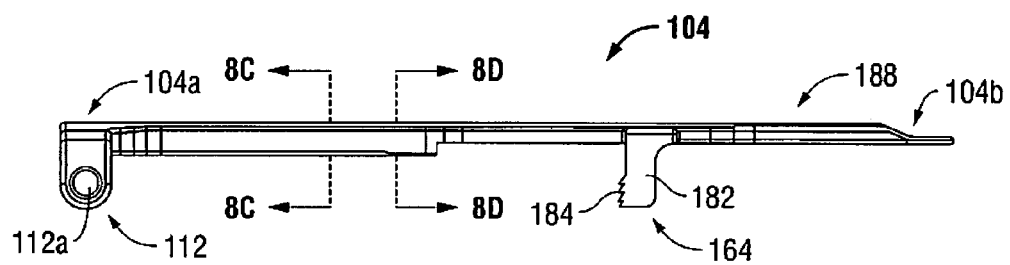
FIG. 8A is a side elevational view of a second elongate member of the sled shown in FIG. 1A.
Figure 8B:
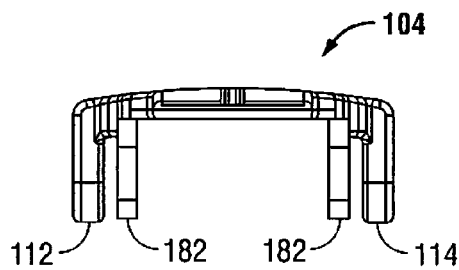
FIG. 8B is a front view of the second elongate member shown in FIG. 8A.
Figure 8C:
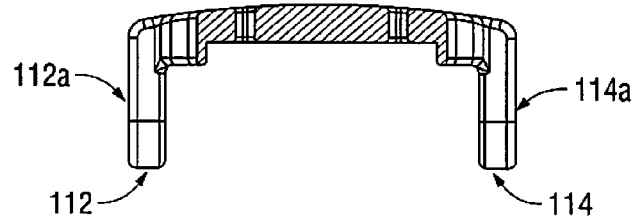
FIG. 8C is a front cross-sectional view of the second elongate member shown in FIG. 8A taken along section line E-E of FIG. 8A.
Figure 8D:
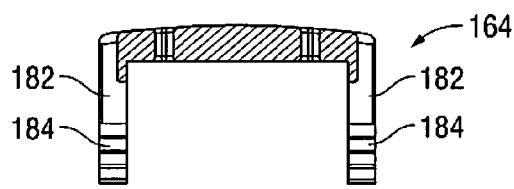
FIG. 8D is a front cross-sectional view of the second elongate member shown in FIG. 8A taken along section line F-F of FIG. 8A.

In one embodiment, a pivot mechanism 106 pivotably interconnects first and second members 102, 104. Pivot mechanism 106 includes two protrusions 108, 110 transversely extending from first elongate member 102, as seen in FIG. 7C. These protrusions 108, 110 are positioned at opposing sides of first elongate member 102. Pivot mechanism 106 additionally includes two protrusions 112, 114 transversely extending from second elongate member 104, as illustrated in FIG. 8C. Protrusions 112, 114 are located at opposite sides of a proximal portion 104a of second elongate member 104. Each protrusion 108, 110, 112, 114 has a corresponding hole 108a, 110a, 112a, 114a adapted to receive a pivot pin 116. In particular, holes 108a and 112a are aligned with each other to allow passage of pivot pin 116 therethrough. Similarly, holes 110a and 114a are aligned with each to allow passage of pivot pin 116 therethrough. In the embodiment depicted in FIG. 1A, a pivot pin 116 extends through holes 108a and 112a and pivotably interconnects protrusion 108 of first elongate member 102 and protrusion 112 of second elongate member 104. Another pivot pin 116 extends through holes 110a and 114a and pivotably interconnects protrusion 110 of first elongate member 102 and protrusion 114 of second elongate member 104.

Figure 9:
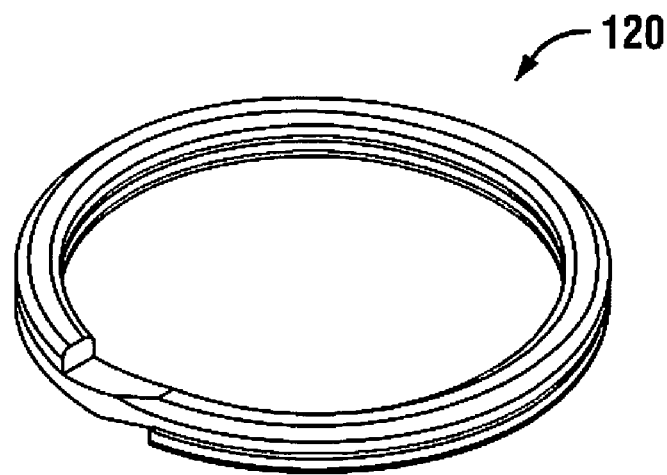
FIG. 9 is a perspective view of a retaining ring of the sled shown in FIG. 1A.
Figure 10:
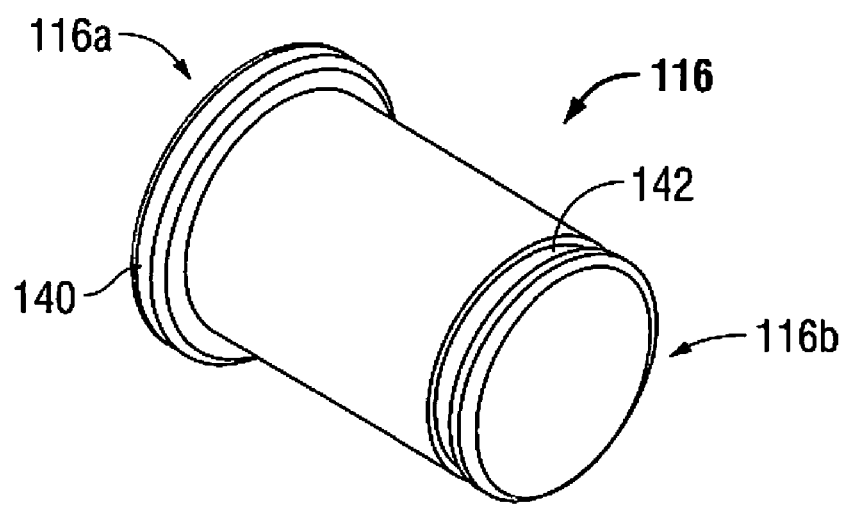
FIG. 10 is a perspective view of a pivot pin of the sled shown in FIG. 1A.

With reference to FIG. 10, both pivot pins 116 have a first end 116a facing an outer portion of the sled 100 and a second end 116b facing an inner portion of sled 100 (FIG. 1A). First end 116a of pivot pin 116 includes a flange 140, whereas the second end 116b of pivot pin 116 has an annular recess 142 formed thereabout. Recess 142 of pivot pin 116 is adapted to receive a retaining ring 120. (See FIG. 9). One retaining ring 120 is positioned on the recess 142 of each pivot pin 116. Both retaining rings 120 assist in the retention of pivot pins 116 in their corresponding holes 108a, 110a, 112a, 114a. Although the drawings show pivot mechanism 106 connecting first elongate member 102 to second elongate member 104, one skilled in the art will recognize that any suitable connecting mechanism may movably couple first elongate member 102 to second elongate member 104.

Figure 1F:
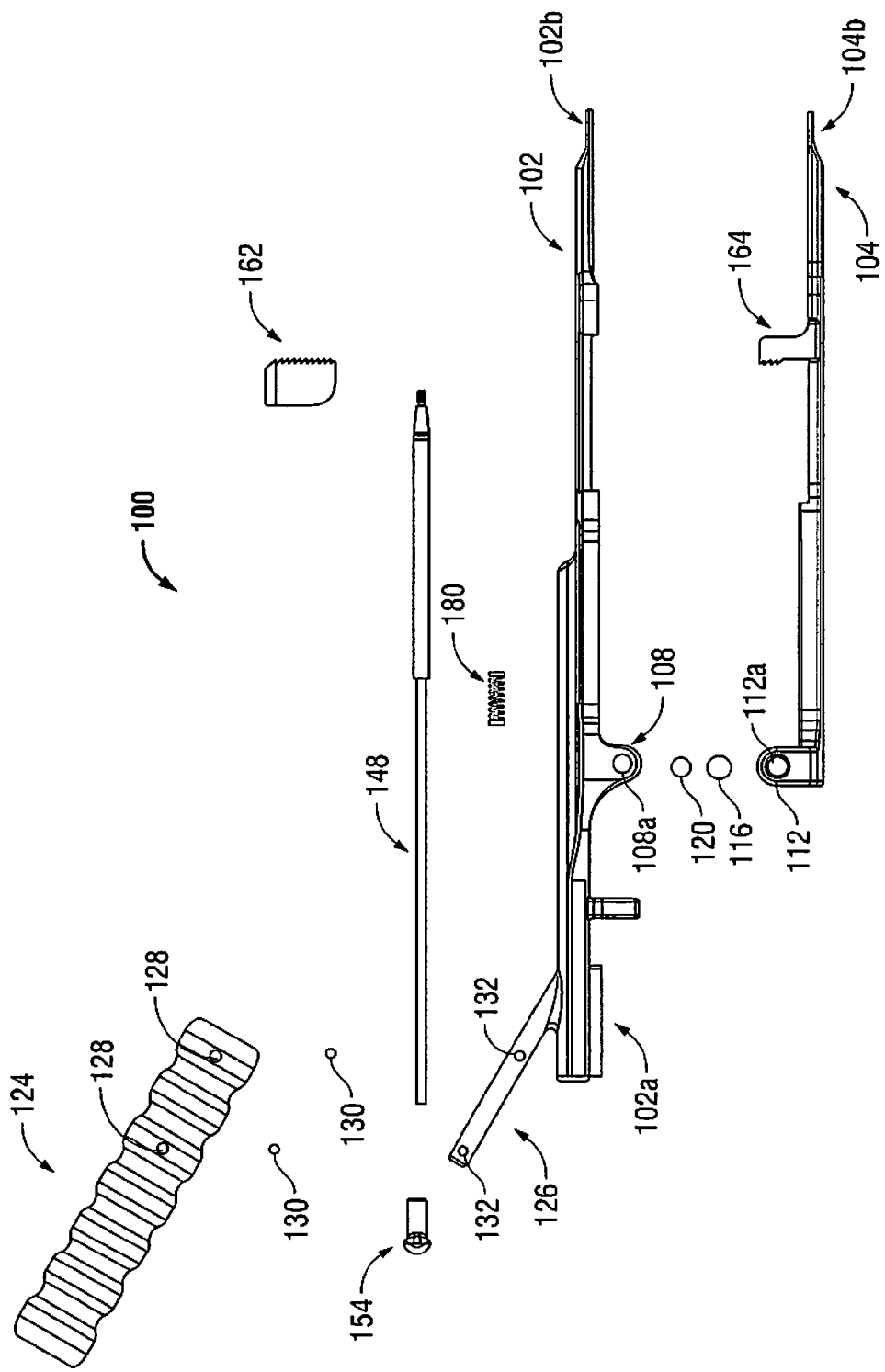
FIG. 1F is a side exploded view of the sled shown in FIG. 1A.
Figure 2:
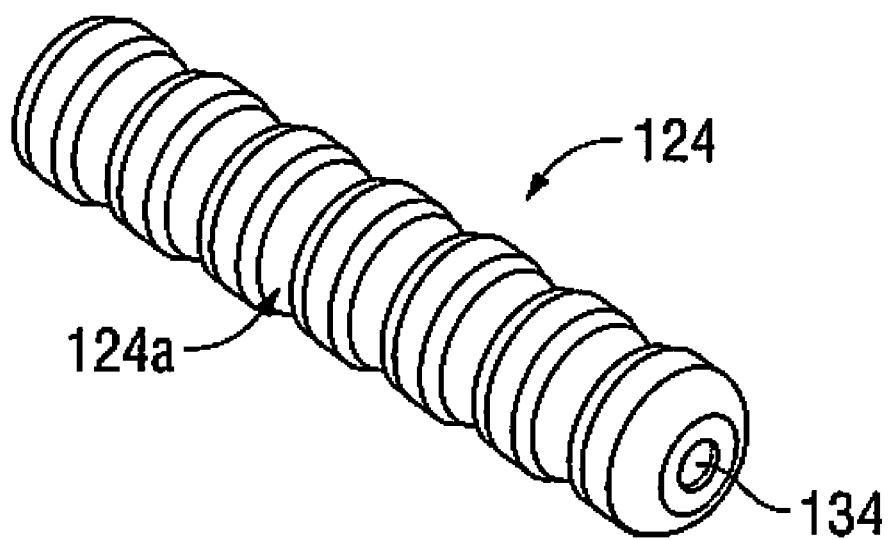
FIG. 2 is a perspective view of a handle of the sled shown in FIG. 1A.
Figure 6:
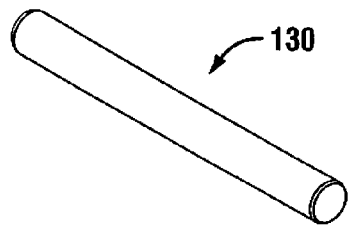
FIG. 6 is a perspective view of a support pin of the sled shown in FIG. 1A.

With reference to FIGS. 1F, 2 and 6, sled 100 further includes a handle 124 operatively secured to first elongate member 102. Alternatively, handle 124 can be operatively fixed to second elongate member 104. In the depicted embodiment, first elongate member 102 has an angled supporting member 126 extending from a proximal portion 102a thereof. As illustrated in FIG. 2, handle 124 has an ergonomic external contour with recesses 124a (it looks like there is a 124 also pointing to the recess feature) strategically positioned along its length. Internally, handle 124 includes a bore 134 extending therethrough. Bore 134 is configured to receive supporting member 126. Support member 126 includes two openings 132 aligned with openings 128 of handle 124. Openings 128, 132 are configured to receive support pins 130. Support pins 130 connect handle 124 to support member 126 and have a cylindrical shape as illustrated in FIG. 6. Nonetheless, a person skilled in the art will recognize that support pins 130 may have any other suitable shape. In fact, the present disclosure contemplates that handle 124 can be fixed to support member 126 by any suitable means such as crimping, adhesives, and welding. In the embodiment shown in FIG. 1F, support pins 130 extend through openings 128 and 132, thereby securing handle 124 to supporting member 126 on the proximal portion 102a of first elongate member 102.

Referring to FIGS. 7A-7E, the proximal portion 102a of first elongate member 102 also includes a guide 136 having an arched-shaped body 138. Arched-shaped body 138 is designed for slidably receiving any suitable surgical instrument such as a spinal implant inserter. During use, guide 136 facilitates the positioning and insertion of a surgical instrument through sled 100.

Besides guide 136, first elongate member 102 has a bore 144 disposed along an outer surface thereof. Bore 144 extends from proximal portion 102a to a location separated from the distal portion 102b of first elongate member 102. An uncovered channel 146 follows bore 144. Bore 144 and channel 146 are disposed longitudinally aligned with each other and both are configured to receive a slider bar 148.

Figure 3A:
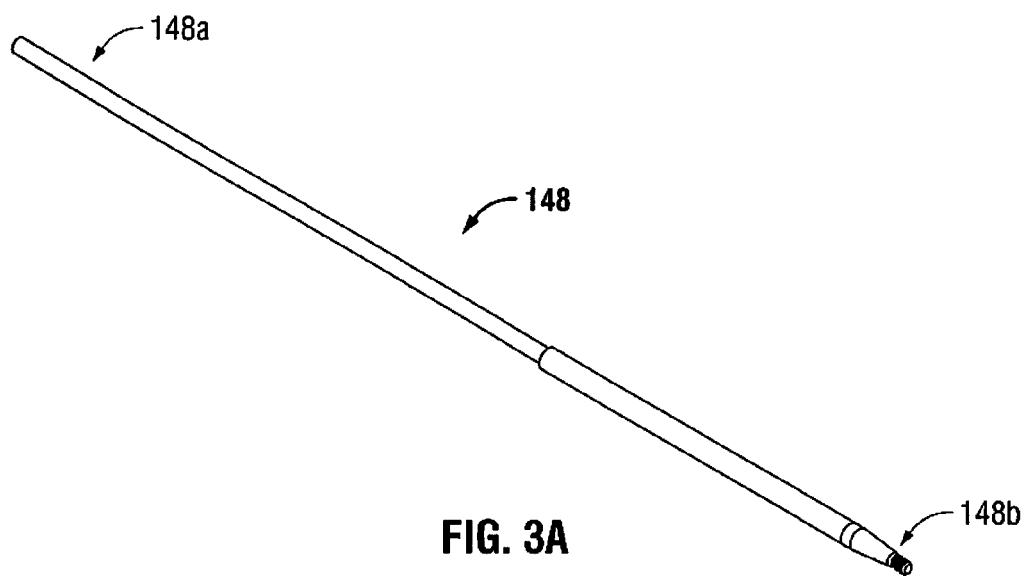
FIG. 3A is a perspective view of a slider bar of the sled shown in FIG. 1A.
Figure 3B:
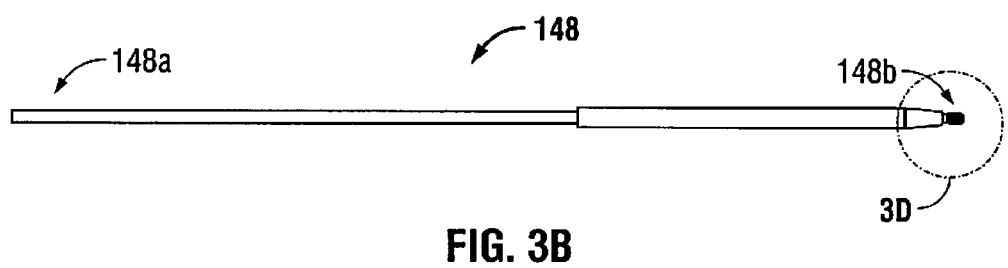
FIG. 3B is a side elevational view of the slider bar shown in FIG. 3A.
Figure 3C:
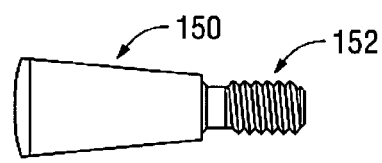
FIG. 3C is an enlarged side view of detail B of the slider bar shown in FIG. 3B.
Figure 3D:
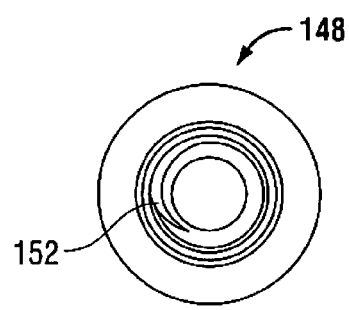
FIG. 3D is a front view of the slider bar shown in FIG. 3A.

With reference to FIGS. 3A-3D, slider bar 148, which is slidably positioned in bore 144 and channel 146, is an elongate structure including a proximal end 148a and a distal end 148b. A spring 180 (FIG. 1F), or any suitable biasing member, is positioned within bore 144 to bias slider bar 148 distally. As shown in FIG. 3A, slider bar 148 has different cross-sectional areas along its length. Distal end 148b of slider bar 148 has a tapered portion 150 and a threaded tip 152. Threaded tip 152 is adapted to be inserted into a portion of a locking mechanism 160 (FIG. 1B). Proximal portion 148a of slider bar 148 is configured to be attached to a knob 154 (FIG. 1A).

With reference to FIGS. 5A-5D, knob 154 has a T-shaped body 156 including an opening 158 partially disposed therethrough. Opening 158 is adapted to receive the proximal portion 148a of slider bar 148 (FIG. 3A). In operation, a user axially moves slider bar 148 by pulling or pushing knob 154. Also, an operator unscrews the threaded tip 152 from locking mechanism 160 (see FIG. 1E) by rotating knob 154. Although the drawings show a knob having a particular shape, the present disclosure envisions knobs having any other suitable shapes so long as it facilitates rotation and longitudinal movement of slider bar 148.

As discussed above and with reference to FIGS. 1A and 1B, a distal end 148b of slider bar 148 is adapted to be inserted into a locking mechanism 160. In use, locking mechanism 160 holds first and second elongate members 102, 104 in position while a surgeon inserts a spinal implant between vertebral bodies. The present disclosure contemplates that sled 100 may have any suitable locking mechanism. Nevertheless, in certain embodiments, locking mechanism 160 is a ratchet-type lock. As illustrated in FIG. 1B, locking mechanism 160 includes a first section 162 disposed in mechanical cooperation with slider bar 148 and a second section 164 operatively coupled to second elongate member 104. First section 162 of locking mechanism 160 partially surrounds a portion of first elongate member 102.

Figure 4A:
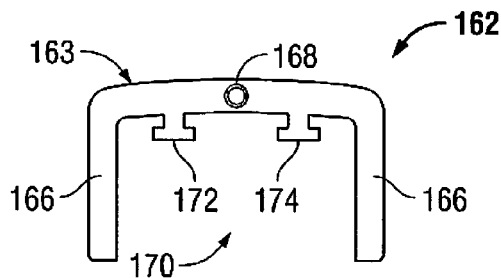
FIG. 4A is a rear view of a portion of a locking mechanism of the sled shown in FIG. 1A.
Figure 4B:
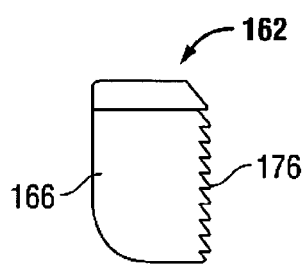
FIG. 4B is a side view of the portion of the locking mechanism shown in FIG. 4A.
Figure 4C:
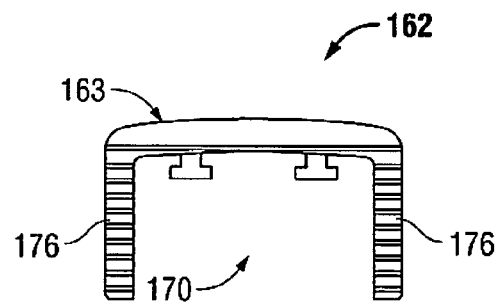
FIG. 4C is a front view of the portion of the locking mechanism shown in FIG. 4A.
Figure 4D:
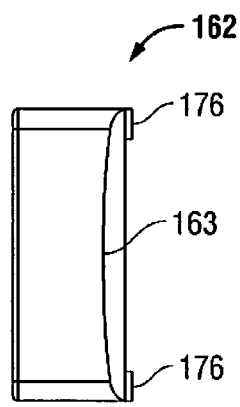
FIG. 4D is a top view of the portion of the locking mechanism shown in FIG. 4A.
Figure 4E:
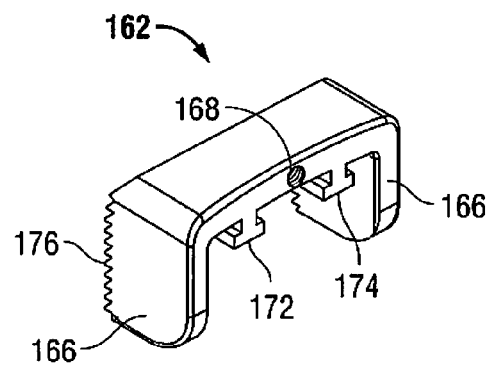
FIG. 4E is a rear perspective view of the portion of the locking mechanism shown in FIG. 4A.
Figure 5A:
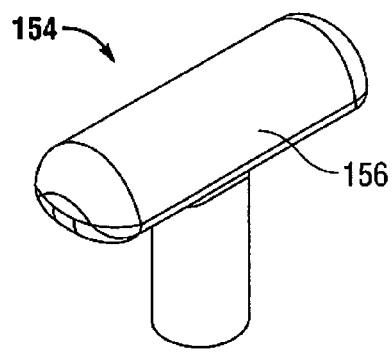
FIG. 5A is a perspective view of a knob of the sled shown in FIG. 1A.
Figure 5B:
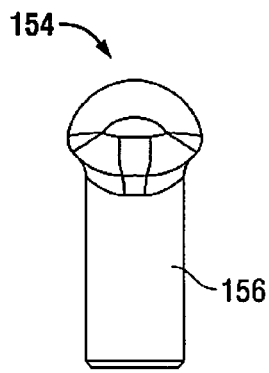
FIG. 5B is a side view of the knob shown in FIG. 5A.
Figure 5C:
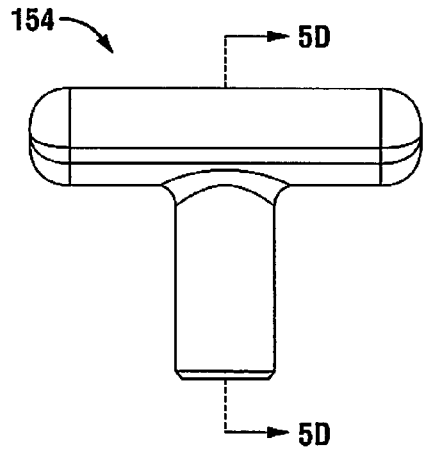
FIG. 5C is a front view of the knob shown in FIG. 5A.
Figure 5D:
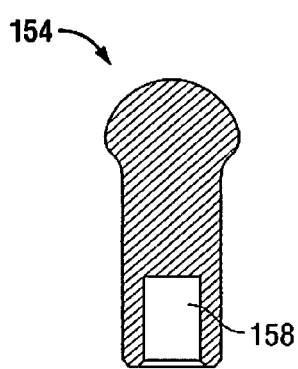
FIG. 5D is a side cross-sectional view of the knob shown in FIG. 5A taken along section line C-C of FIG. 5C.

With reference to FIGS. 4A-4E, first section 162 of locking mechanism 160 includes a bridge portion 163 interconnecting two legs 166 at opposite sides. Bridge portion 163 has a threaded bore 168 extending at least partially therethrough and a slider 170 located at a bottom surface of bridge portion 163. When assembled, threaded bore 168 threadably engages threaded tip 152 of slider bar 148 (FIG. 1A). Slider 170 includes a pair of guiding members 172, 174 configured to slide through longitudinal slots 178 (see FIGS. 7D & 7E) defined along a portion of the length of first elongate member 102. Guiding members 172, 174 are T-shaped protrusions extending from the bottom surface of bridge section 163, as shown in FIG. 4A. The present disclosure, however, envisions guiding members having other suitable configurations. During use, when slider bar 148 is engaged with first section 162 of locking mechanism 160, an axial motion of slider bar 148 causes first section 162 to slide along at least a portion of the length of first elongate member 102.

As previously discussed, bridge portion 163 interconnects a pair of legs 166. Legs 166 transversely extend from opposite sides of bridge portion 163 and each include teeth 176 facing the distal portion 102b of first elongate member 102. Teeth 176 of first section 162 are configured to engage teeth 184 of a second section 164 of locking mechanism 160 (FIG. 8A).

With reference to FIGS. 8A-8D, second section 164 of locking member 160 is formed by a pair of legs 182 fixed to second elongate member 104. Legs 182 transversely extend from second elongate member 104 and each have teeth 184 facing a proximal portion 104a of second elongate member 104. Teeth 184 are configured to engage teeth 176 of first section 162 of locking mechanism 160. During use, when teeth 176 and 184 are engaged with one another, first and second elongate member 102, 104 are inhibited from moving towards each other, while still being capable of moving away from each other. That is, engagement of the first and second teeth 176, 184 allows movement of the first and second jaw members 186, 188 toward the first position while inhibiting movement of the first and second jaw members 186, 188 toward the second position.

With reference to FIGS. 1A and 1B, first and second elongate members 102, 104 each include a jaw member 186, 188 at their respective distal portions 102b, 104b. In operation, jaw members 186, 188 move with respect to one another about pivot mechanism 106. Particularly, jaw members 186, 188 are capable of moving between an open position and an approximated position when first and second elongate members are moved with respect to each other. Notwithstanding the foregoing, jaw members 186, 188 are fixed into a particular position by engaging first section 162 to the second section 164 of locking mechanism 160, thereby maintaining a spaced apart relationship between the jaw members 186, 188. Each jaw member 186, 188 has a contacting surface 186a, 188a adapted to hold a spinal implant or the like.

Sled 100 facilitates insertion of a spinal implant, such as an interbody implant device, between vertebral bodies during spinal fusion surgery. In operation, a healthcare professional removes deceased intervertebral material before inserting the distal portions 102b, 104b of first and second elongate members 102, 104 between adjacent vertebrae. After extracting the damaged intervertebral material, the healthcare professional inserts at least a portion of jaw members 186, 188 into a space between neighboring vertebrae.

Once the first and second elongate members 102, 104 are in the second or approximated position, the healthcare professional inserts at least a portion of jaw members 186, 188 into an intervertebral space. Thereafter, jaw members 186, 188 are then separated from each other, i.e. moved to the first or open position, by inserting a trial or an implant through sled 100 and into the target intervertebral space. The healthcare professional uses an implant inserter or the like to position the trial in the desired site. When the trial moves through sled 100, jaw members 186, 188 move from the second or approximated position to the first or open position as a result of the trial spreading the jaw members 186, 188 apart. As the jaw members 186, 188 move toward the first or open position, the adjacent vertebrae move away from each other. The trial helps the healthcare professionals size the volume of the target intervertebral space. After sizing the intervertebral space, the healthcare professional locks locking mechanism 160 by axially moving knob 154 in a distal direction until teeth 176 of first section 162 engage teeth 184 of second section 164 of locking mechanism 160, thereby inhibiting jaw members 186, 188 from moving toward each other. Alternatively, the locking mechanism can be engaged as the elongate members are spread apart, so that the locking mechanism ratchets open as the trial or implant is inserted. Afterwards, the trial is removed from the intervertebral space. While the healthcare professional removes the trial from the sled 100, jaw members 186, 188 remain in the first or open position, because first and second elongate members 102, 104 are locked into position by locking mechanism 160. A spinal implant, such as an interbody implant device, is then inserted through sled 100 and into the intervertebral space. Once the spinal implant has been inserted into the intervertebral space, the healthcare professional removes sled 100 from the surgical site. To remove jaw members 186, 188 from the intervertebral space, the healthcare professional should unlock locking mechanism 160. Locking mechanism 160 is unlocked by moving slider bar 148 proximally through knob 154. The proximal translation of slider bar 148 disengages teeth 176 from teeth 184, thereby unlocking locking mechanism 160.

What is claimed is:
1. An apparatus for inserting a spinal implant, comprising:
  a first elongate member including a first jaw member disposed at a distal portion thereof, wherein the first jaw member defines a first longitudinal axis;
  a second elongate member operatively connected to the first elongate member and including a second jaw member disposed at a distal portion thereof, the second jaw member defining a second longitudinal axis, wherein the first and second elongate members are adapted to move the first and second jaw members between a first position where the first and second longitudinal axes are oriented substantially parallel to each other and a second position where the first and second longitudinal axes are oriented at an acute angle with respect to each other; and a locking mechanism adapted to releasably fix a relative position of the first and second elongate members, the locking mechanism including:

a first section slidably disposed on the first elongate member, the first section including a guiding member adapted for facilitating translation along the first elongate member; and a second section affixed to the second elongate member, wherein the first elongate member includes a slot extending therealong, the slot being configured for slidably receiving the guiding member and guiding the translation of the first section of the locking mechanism along the first elongate member.

2. The apparatus according to claim 1, further comprising a pivot mechanism interconnecting the first and second elongate members, wherein the pivot mechanism facilitates pivotal movement of the first and second elongate members with respect to each other.

3. The apparatus according to claim 1, further comprising a slider bar slidably disposed on the first elongate member.

4. The apparatus according to claim 3, wherein the slider bar is operatively coupled to the first section of the locking mechanism such that translating the slider bar effects a translation of the first section of the locking mechanism along the first elongate member.

5. The apparatus according to claim 3, wherein the slider bar includes a threaded tip disposed at a distal end thereof and the first section of the locking mechanism includes a threaded bore configured to threadably receive the threaded tip of the slider bar.

6. The apparatus according to claim 3, wherein the first elongate member includes a channel adapted to slidably receive the slider bar.

7. The apparatus according to claim 6, wherein the first elongate member includes a bore longitudinally aligned with the channel, the bore being adapted for slidably receiving the slider bar.

8. The apparatus according to claim 3, wherein the slider bar includes a knob disposed at a proximal end thereof, the knob being adapted for facilitating rotation and translation of the slider bar.

9. The apparatus according to claim 3, further comprising a biasing member operatively coupled to the slider bar, wherein the biasing member is adapted to bias the slider bar distally.

10. The apparatus according to claim 1, wherein the first section of the locking mechanism includes a first set of teeth and the second section of the locking mechanism includes a second set of teeth configured to engage the first sets of teeth such that engagement of the first and second sets of teeth allows movement of the first and second jaw members toward the first position while inhibiting movement of the first and second jaw members toward the second position.

11. The apparatus according to claim 10, wherein the first section of the locking mechanism includes first and second legs, the first set of teeth formed on each of the first and second legs.

12. The apparatus according to claim 10, wherein the second section of the locking mechanism includes first and second legs, the second set of teeth formed on each of the first and second legs.

13. The apparatus according to claim 1, wherein the first section of the locking mechanism is releasably positioned on the first elongate member.

14. The apparatus according to claim 1, wherein the second section of the locking mechanism is monolithically formed on the second elongate member.

15. The apparatus according to claim 1, further comprising a guide for facilitating positioning and insertion of a surgical instrument through the apparatus.

16. An apparatus for inserting a spinal implant, comprising:

a first elongate member including a first jaw member disposed at a distal portion thereof, wherein the first jaw member defines a first longitudinal axis;

a second elongate member operatively connected to the first elongate member and including a second jaw member disposed at a distal portion thereof, the second jaw member defining a second longitudinal axis, wherein the first and second elongate members are adapted to move the first and second jaw members between a first position where the first and second longitudinal axes are oriented substantially parallel to each other and a second position where the first and second longitudinal axes are oriented at an acute angle with respect to each other; and a locking mechanism adapted to releasably fix a relative position of the first and second elongate members, the locking mechanism including:

a first section slidably disposed on the first elongate member; and a second section affixed to the second elongate member, wherein the first section of the locking mechanism includes a first set of teeth and the second section of the locking mechanism includes a second set of teeth configured to engage the first set of teeth such that engagement of the first and second sets of teeth allows movement of the first and second jaw members toward the first position while inhibiting movement of the first and second jaw members toward the second position.

17. The apparatus according to claim 16, wherein the first section of the locking mechanism includes first and second legs, the first set of teeth formed on each of the first and second legs.

18. The apparatus according to claim 16, further comprising a slider bar slidably disposed on the first elongate member.

19. The apparatus according to claim 18, wherein the slider bar is operatively coupled to the first section of the locking mechanism such that translating the slider bar effects a translation of the first section of the locking mechanism along the first elongate member.

20. The apparatus according to claim 18, wherein the slider bar includes a threaded tip disposed at a distal end thereof and the first section of the locking mechanism includes a threaded bore configured to threadably receive the threaded tip of the slider bar.

21. The apparatus according to claim 18, wherein the first elongate member includes a channel adapted to slidably receive the slider bar.

22. The apparatus according to claim 21, wherein the first elongate member includes a bore longitudinally aligned with the channel, the bore being adapted for slidably receiving the slider bar.

23. The apparatus according to claim 18, wherein the slider bar includes a knob disposed at a proximal end thereof, the knob being adapted for facilitating rotation and translation of the slider bar.

24. The apparatus according to claim 18, further comprising a biasing member operatively coupled to the slider bar, wherein the biasing member is adapted to bias the slider bar distally.

25. The apparatus according to claim 16, wherein the first section of the locking mechanism includes a guiding member adapted for facilitating translation along the first elongate member.

26. The apparatus according the claim 25, wherein the first elongate member includes a slot extending therealong, the slot being configured for slidably receiving the guiding member and guiding the translation of the first section of the locking mechanism along the first elongate member.

27. The apparatus according to claim 16, wherein the first section of the locking mechanism is releasably positioned on the first elongate member.

28. The apparatus according to claim 16, wherein the second section of the locking mechanism is monolithically formed on the second elongate member.

29. The apparatus according to claim 16, further comprising a guide for facilitating positioning and insertion of a surgical instrument through the apparatus.

30. The apparatus according to claim 16, wherein the second section of the locking mechanism includes first and second legs, the second set of teeth formed on each of the first and second legs.

31. The apparatus according to claim 16, further comprising a pivot mechanism interconnecting the first and second elongate members, wherein the pivot mechanism facilitates pivotal movement of the first and second elongate members with respect to each other.

* * * * *